United States Patent [19]

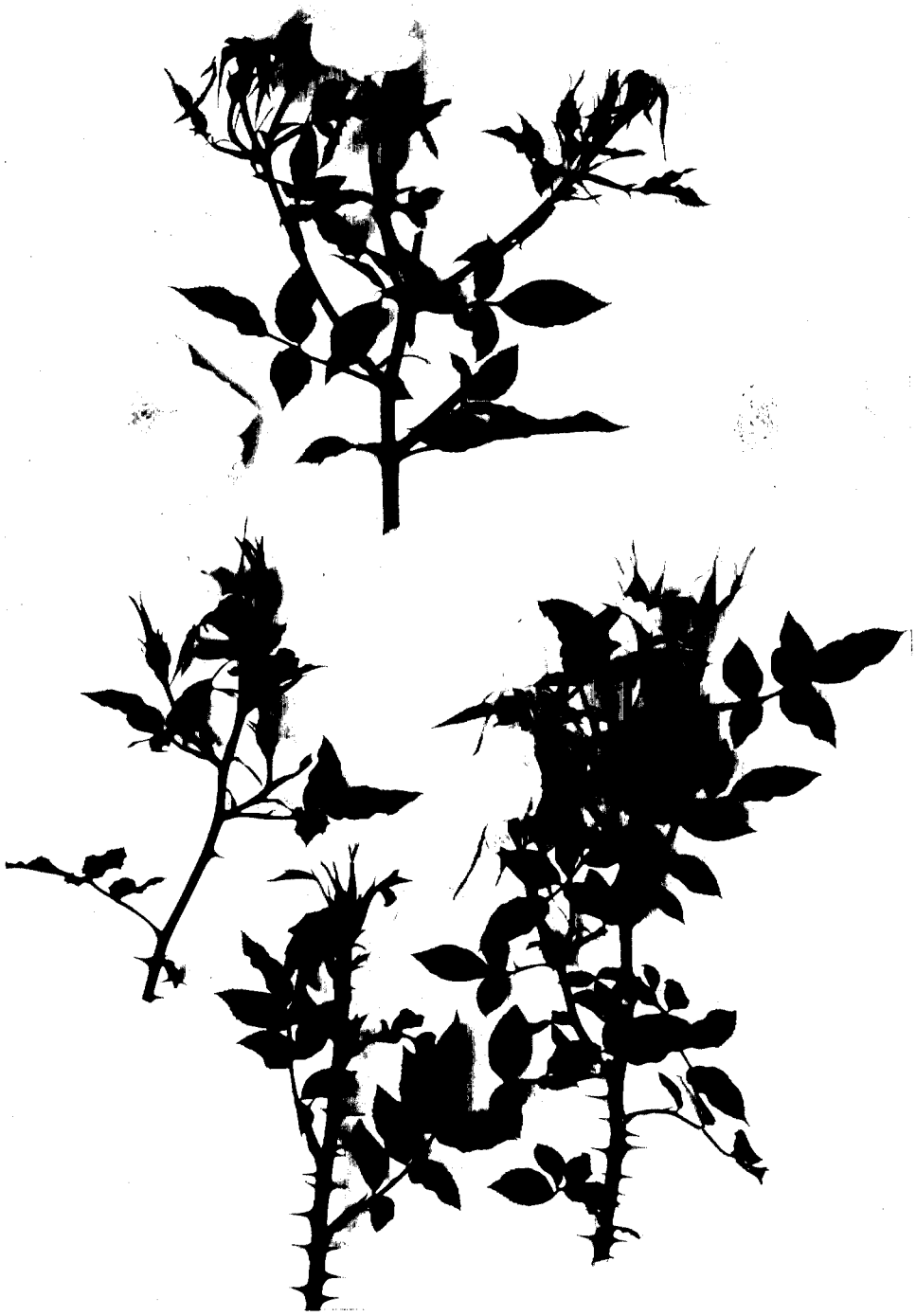

Warriner

[11] Patent Number: Plant 5,557

[45] Date of Patent: Sep. 17, 1985

[54] ROSE PLANT JACLITE

[75] Inventor: William A. Warriner, Tustin, Calif.

[73] Assignee: Jackson & Perkins Comany, Medford, Oreg.

[21] Appl. No.: 549,300

[22] Filed: Nov. 7, 1983

[51] Int. Cl.[3] ..... A01H 5/00

[52] U.S. Cl. ..... Plt./8

[58] Field of Search ..... Plt./8

*Primary Examiner*—James R. Feyrer

*Attorney, Agent, or Firm*—Klarquist, Sparkman, Campbell, Leigh & Whinston

[57] ABSTRACT

A miniature rose variety having compact, spreading plant with dwarf growth habit, yellowish buds opening to 2½" white flowers, mild fragrance, resistance to powdery mildew, and many straight thorns.

1 Drawing Figure

This present invention relates to a new and distinct variety of rose plant of the miniature class which was originated by me by crossing the variety Bon Bon, U.S. Plant Pat. No. 3,555, with the variety Calgold, U.S. Plant Pat. No. 4,230.

The primary objective of this breeding was to produce a new rose variety combining the plant habit of Bon Bon with miniature characteristics of Calgold. This objective was substantially achieved along with other desirable improvements as evidenced by the following unique combination of characteristics which are outstanding in the new variety and which distinguish it from its parents, as well as from all other varieties of which I am aware:

1. Its compact, spreading plant habit.
2. Dwarfness, mostly under two feet in height.
3. Yellowish buds opening to white, 2½" flowers.
4. Mild fragrance.
5. Resistance to powdery mildew.
6. Many straight thorns.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bon Bon, U.S. Plant Pat. 3,555.

*Pollen parent.*—Calgold, U.S. Plant Pat. 4,230.

Classification:

*Botanical.*—Rosa hybrid.

*Commercial.*—Miniature.

FLOWER

Observations made from specimens grown in August at Irvine, Calif.

Blooming habit: Recurrent.

Bud:

*Size.*—¾" when petals start to unfurl.

*Form.*—Pointed ovoid, broad base.

*Color.*—When sepals first divide, Yellow 11C to 11D. When half blown; upper side of petals white; lower side of petals white.

*Sepals.*—Color; Outer surface Green 138A, nearly smooth with very few glands and pubescence. Three appendaged sepals lightly appendaged. Two unappendaged sepals hairy edged.

*Receptacle.*—Color: Green 138A. Shape: Funnel. Size: Large, broad, relative to flower size. Surface: Smooth.

*Peduncle.*—Length: Short. Surface: Slightly glandular. Color: Light green. Strength: Stiff, erect.

*Opening.*—Petals fall outward slowly.

Bloom:

*Size.*—Medium. Average open size: 2½".

*Borne.*—Singly and in clusters, flat.

*Stems.*—Short, strong.

*Form.*—When first open, flat. Permanence: Retains its form to the end.

*Petalage.*—Number of petals under normal conditions: 30–35.

*Color.*—Center of flower: Upper side of petals white; reverse side of petals white; base of petals very lightly tinted yellow. General tonality from a distance, white.

*Variegations.*—None.

*Discoloration.*—General tonality at end of first day: No change. Third day: Stays white.

*Fragrance.*—Mild.

Petals:

*Texture.*—Thin.

*Shape.*—Oblanceolate.

*Form.*—Tips slightly recurved.

*Arrangement.*—Imbricated. Petaloids in center, many.

*Persistence.*—Drop off cleanly.

*Lastingness.*—On the plant, long. As cut flower, long.

Reproductive parts:

*Anthers.*—Medium, many. Color:Yellow. Arrangement: Regular around styles and mixed with petaloids.

*Filaments.*—Color: White.

*Pollen.*—Lemon Yellow.

*Styles.*—Color: Reddish.

*Stigmas.*—Color: Red.

PLANT

Form: Bush.

Growth: Vigorous, dwarf, sprawly. Generally under 2′ at Irvine, Calif.

Foliage: Number of leaflets on normal mid-stem leaves: 7.

*Size.*—Medium.

*Quantity.*—Normal.

*Color.*—New foliage: Green 139A with purplish overlay. Old foliage: Medium green.

Leaflets:

*Shape.*—Oval pointed.

*Texture.*—Upper side: Leathery.

*Edge.*—Serrated.

*Serration.*—Single, small.

*Petiole.*—Rachis, Color: Green. Underside: Prickles.

*Stipules.*—Long, bearded.

*Disease resistance.*—Resistant to mildew, susceptible to blackspot under normal growing conditions at Irvine, Calif.

Wood:

*New wood.*—Color, Reddish. Bark: Smooth.

*Old wood.*—Color: Green. Bark: Smooth.

Prickles:

*Quantity.*—On main stalks from base, many. On laterals from stalk, many.

*Form.*—Long, straight.

*Color when young.*—Brown.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its dwarf plant, mildew resistance, thorny stems, white flowers with a mild fragrance.

* * * * *